(12) United States Patent
Furfine et al.

(10) Patent No.: US 8,092,803 B2
(45) Date of Patent: Jan. 10, 2012

(54) VEGF ANTAGONIST FORMULATIONS FOR INTRAVITREAL ADMINISTRATION

(75) Inventors: Eric Furfine, Concord, MA (US); Daniel Dix, LaGrangeville, NY (US); Kenneth S. Graham, Pleasant Valley, NY (US); Kelly Frye, Pomona, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 7 days.

(21) Appl. No.: 12/833,417

(22) Filed: Jul. 9, 2010

(65) Prior Publication Data

US 2011/0257601 A1 Oct. 20, 2011

Related U.S. Application Data

(60) Continuation of application No. 12/560,885, filed on Sep. 16, 2009, now Pat. No. 7,807,164, which is a division of application No. 11/818,463, filed on Jun. 14, 2007, now Pat. No. 7,608,261.

(60) Provisional application No. 60/814,484, filed on Jun. 16, 2006.

(51) Int. Cl.
*A61K 38/18* (2006.01)
*C07K 14/71* (2006.01)

(52) U.S. Cl. .................. 424/134.1; 424/192.1; 514/1.1; 514/8.1; 530/350

(58) Field of Classification Search ........................ None
See application file for complete search history.

(56) References Cited

U.S. PATENT DOCUMENTS

| 6,100,071 A | 8/2000 | Davis-Smyth et al. |
| 6,897,294 B2 | 5/2005 | Davis-Smyth et al. |
| 7,052,691 B2 | 5/2006 | Sleeman et al. |
| 2005/0281831 A1 | 12/2005 | Davis-Smyth et al. |
| 2006/0217311 A1 | 9/2006 | Dix et al. |

FOREIGN PATENT DOCUMENTS

| WO | WO 2005/000895 | 1/2005 |
| WO | WO 2006/047325 | 5/2006 |
| WO | WO 2006/104852 | 10/2006 |

*Primary Examiner* — Christine J Saoud
*Assistant Examiner* — Jon M Lockard
(74) *Attorney, Agent, or Firm* — Joseph E. Zahner

(57) ABSTRACT

Ophthalmic formulations of a vascular endothelial growth factor (VEGF)-specific fusion protein antagonist are provided suitable for intravitreal administration to the eye. The ophthalmic formulations include a stable liquid formulation and a lyophilizable formulation. Preferably, the protein antagonist has the amino acid sequence shown in SEQ ID NO:4.

19 Claims, No Drawings

VEGF ANTAGONIST FORMULATIONS FOR INTRAVITREAL ADMINISTRATION

CROSS-REFERENCE TO RELATED APPLICATIONS

This application is a continuation application of U.S. patent application Ser. No. 12/560,885, filed 16 Sep. 2009, which is a divisional application of U.S. patent application Ser. No. 11/818,463, filed 14 Jun. 2007, which issued as U.S. Pat. No. 7,608,261 on 27 Oct. 2009, which claims the benefit under 35 U.S.C. §119(e) of U.S. Provisional Application No. 60/814,484, filed 16 Jun. 2006, which applications are each hereby incorporated by reference.

BACKGROUND OF THE INVENTION

1. Field of the Invention

The present invention is directed to pharmaceutical formulations suitable for intravitreal administration comprising agents capable of inhibiting vascular endothelial growth factor (VEGF), and to methods for making and using such formulations. The invention includes liquid pharmaceutical formulations having increased stability, as well as formulations that may be lyophilized and reconstituted for intravitreal administration.

2. Statement of Related Art

Vascular endothelial growth factor (VEGF) expression is nearly ubiquitous in human cancer, consistent with its role as a key mediator of tumor neoangiogenesis. Blockade of VEGF function, by binding to the molecule or its VEGFR-2 receptor, inhibits growth of implanted tumor cells in multiple different xenograft models (see, for example, Gerber et al. (2000) Cancer Res. 60:6253-6258). A soluble VEGF-specific fusion protein antagonist, termed a "VEGF-trap" has been described (Kim et al. (2002) Proc. Natl. Acad. Sci. USA 99:11399-404; Holash et al. (2002) Proc. Natl. Acad. Sci. USA 99:11393-8), which applications are specifically incorporated by reference in their entirety.

Ophthalmic formulations are known, see for example, U.S. Pat. Nos. 7,033,604 and 6,777,429. An ophthalmic formulation of a VEGF antibody is described in U.S. Pat. No. 6,676,941.

Lyophilization (freeze drying under controlled conditions) is commonly used for long-term storage of proteins. The lyophilized protein is substantially resistant to degradation, aggregation, oxidation, and other degenerative processes while in the freeze-dried state (see, for example, U.S. Pat. No. 6,436,897).

BRIEF SUMMARY OF THE INVENTION

Stable formulations of a VEGF-specific fusion protein antagonist are provided. Pharmaceutically acceptable formulations are provided that comprise a VEGF "trap" antagonist with a pharmaceutically acceptable carrier. In specific embodiments, liquid and lyophilized formulations are provided.

In a first aspect, a stable liquid ophthalmic formulation of a VEGF-specific fusion protein antagonist is provided, comprising a fusion protein that comprises a receptor component consisting essentially of an immunoglobulin-like (Ig) domain 2 of a first VEGF receptor and Ig domain 3 of a second VEGF receptor, and a multimerizing component (also termed a "VEGF trap"). In a specific embodiment of the VEGF-specific fusion protein antagonist, the first VEGF receptor is Flt1 and the second VEGF receptor is Flk1 or Flt4. In a more specific embodiment the fusion protein has the amino acid sequence of SEQ ID NO:2 or SEQ ID NO:4. Preferably, the VEGF antagonist is a dimer comprising two fusion proteins of SEQ ID NO:4.

In one aspect, a stable liquid ophthalmic formulation is provided that comprises 1-100 mg/ml VEGF-specific fusion protein antagonist, 0.01-5% of one or more organic co-solvent(s), 30-150 mM of one or more tonicity agent(s), 5-40 mM of a buffering agent, and optionally, 1.0-7.5% of a stabilizing agent, pH between about 5.8-7.0.

In one or more specific embodiments, the organic co-solvent may be polysorbate, for example, polysorbate 20 or polysorbate 80, polyethylene glycol (PEG), for example, PEG 3350, or propylene glycol, or a combination thereof; the tonicity agent may be, for example, sodium chloride or potassium chloride; the stabilizing agent may be sucrose, sorbitol, glycerol, trehalose, or mannitol; and the buffering agent may be, for example, phosphate buffer. In a specific embodiment, the phosphate buffer is a sodium phosphate buffer.

In various embodiments, the organic co-solvent is polysorbate and/or PEG, the stabilizing agent is sucrose, the buffering agent is phosphate buffer, and the tonicity agent is sodium chloride.

More specifically, the stable liquid ophthalmic formulation comprises about 40-50 mg/ml of the VEGF antagonist (SEQ ID NO:4), about 10 mM phosphate buffer, 0.01-3% polysorbate and/or PEG, 40-135 mM sodium chloride, and optionally 5.0% sucrose, pH about 6.2-6.3.

In a specific preferred embodiment, the stable liquid ophthalmic formulation comprises about 50 mg/ml of the VEGF antagonist (SEQ ID NO:4), 10 mM sodium phosphate buffer, 50 mM sodium chloride, 0.1% polysorbate, and 5% sucrose, pH about 6.2-6.3.

In a specific preferred embodiment, the stable liquid ophthalmic formulation comprises about 50 mg/ml of the VEGF antagonist (SEQ ID NO:4), 10 mM sodium phosphate buffer, 50 mM sodium chloride, 3% PEG, and 5% sucrose, pH about 6.2-6.3.

In a specific preferred embodiment, the stable liquid ophthalmic formulation comprises about 40 mg/ml of the VEGF antagonist (SEQ ID NO:4), 10 mM sodium phosphate buffer, 40 mM sodium chloride, 0.03% polysorbate, and 5% sucrose, pH about 6.2-6.3.

In a specific preferred embodiment, the stable liquid ophthalmic formulation comprises about 40 mg/ml of the VEGF antagonist (SEQ ID NO:4), 10 mM sodium phosphate buffer, 135 mM sodium chloride, and 0.03% polysorbate, pH about 6.2-6.3.

In another aspect, a stable liquid ophthalmic formulation is provided that comprises 1-100 mg/ml VEGF-specific fusion protein antagonist; 0.01-5% of one or more organic co-solvent(s); 5-40 mM of a buffering agent; and optionally 30-150 mM of one or more tonicity agent(s) and/or 1.0-7.5% of a stabilizing agent; having a pH between about 5.8-7.0.

In various embodiments, the VEGF antagonist (SEQ ID NO:4) is present at a concentration of about 10 to about 80 mg/ml. In various embodiments, the VEGF antagonist (SEQ ID NO:4) is present at a concentration of about 10, about 20, about 30, about 40, about 50, about 60, about 70, or about 80 mg/ml. In a preferred embodiment, the VEGF antagonist (SEQ ID NO:4) is present at a concentration of about 40 mg/ml.

In another embodiment, the stabilizing agent is selected from one or more of sucrose, sorbitol, glycerol, trehalose, and mannitol.

In another embodiment, the organic co-solvent is selected from one or more of polysorbate, for example, polysorbate 20 or polysorbate 80, polyethylene glycol (PEG), for example, PEG 3350, and propylene glycol.

In another embodiment, the buffer is a phosphate buffer, for example, sodium phosphate.

In another embodiment, the tonicity agent is a salt, for example, sodium chloride.

In one embodiment, the stable liquid ophthalmic formulation comprises 10 mM sodium phosphate buffer, about 0.03 to about 0.1% polysorbate and/or about 3% PEG or propylene glycol, about 40 mM sodium chloride, and about 5% sucrose. In a specific embodiment, the stable liquid ophthalmic formulation comprises 10 mM sodium phosphate buffer, about 0.03% polysorbate, about 40 mM sodium chloride, and about 5% sucrose. In another specific embodiment, the pH of the formulation is about 6.2 to about 6.3. In another specific embodiment, the pH is achieved by mixing mono- and dibasic sodium phosphate to the desired pH without acid/base titration.

In a specific embodiment, the stable liquid ophthalmic formulation consists essentially of a VEGF antagonist (SEQ ID NO:4) at 40 mg/ml, 10 mM sodium phosphate buffer, polysorbate at 0.03%, sodium chloride at 40 mM, and sucrose at 5%, pH 6.2-6.3.

In another aspect, a stable liquid ophthalmic formulation is provided that comprises about 10 to about 80 mg/ml VEGF antagonist, about 10 mM sodium phosphate buffer, about 0.03% polysorbate, and about 135 mM sodium chloride, pH 6.2 to 6.3.

In various embodiments, the VEGF antagonist (SEQ ID NO:4) is present at a concentration of about 10 to about 80 mg/ml. In various embodiments, the VEGF antagonist (SEQ ID NO:4) is present at a concentration of about 10, about 20, about 30, about 40, about 50, about 60, about 70, or about 80 mg/ml. In a specific embodiment, the VEGF antagonist (SEQ ID NO:4) is present at a concentration of about 40 mg/ml.

In one embodiment, the stable liquid ophthalmic formulation comprises 40 mg/ml of VEGF antagonist (SEQ ID NO:4), 10 mM sodium phosphate buffer, 0.03% polysorbate, and 135 mM sodium chloride at pH 6.2-6.3. In a specific embodiment, the stable liquid ophthalmic formulation consists essentially of 40 mg/ml of VEGF antagonist (SEQ ID NO:4), 10 mM sodium phosphate buffer, 0.03% polysorbate, and 135 mM sodium chloride at pH 6.2-6.3.

In another aspect, a lyophilizable formulation of a VEGF antagonist is provided, wherein upon lyophilization followed by reconstitution, a stable liquid ophthalmic formulation as described herein is obtained.

In another aspect, a lyophilizable formulation of a vascular endothelial growth factor (VEGF)-specific fusion protein antagonist is provided, comprising 5-50 mg/ml of the VEGF antagonist, 5-25 mM buffer, such as phosphate buffer, 0.01 to 0.15% of one or more of an organic co-solvent, such as polysorbate, propylene glycol and/or PEG, and optionally 1-10% of a stabilizing agent such as sucrose, sorbitol, trehalose, glycerol, or mannitol, pH about 5.8-7.0. In various embodiments, the VEGF antagonist (SEQ ID NO:4) is present at about 5, about 10, about 20, about 30, or about 40 mg/ml. In a specific embodiment, the lyophilizable ophthalmic formulation of the invention comprises 20 mg/ml of the VEGF antagonist, 10 mM sodium phosphate buffer, 0.03% polysorbate, 0.1% PEG, and 2.5% sucrose, pH about 6.2-6.3. In further embodiments, the lyophilizable formulation further comprises sodium chloride. In a specific embodiment, the sodium chloride is present at a concentration of about 20 mM. In another specific embodiment, the sodium chloride is present at a concentration of about 67.5 mM.

In another specific embodiment, the lyophilizable ophthalmic formulation of the invention comprises 20 mg/ml of the VEGF antagonist, 5 mM sodium phosphate buffer, 0.015% polysorbate, 20 mM sodium chloride, and 2.5% sucrose, pH about 6.2-6.3.

In another embodiment, the lyophilizable ophthalmic formulation comprises 5 mg/ml, 10 mg/ml, or 40 mg/ml VEGF antagonist, 5 mM sodium phosphate buffer, 0.015% polysorbate, 20 mM sodium chloride, and 2.5% sucrose, at pH 6.2-6.3. In a specific embodiment, the lyophilizable ophthalmic formulation consists essentially of 5 mg/ml, 10 mg/ml, or 40 mg/ml VEGF antagonist (SEQ ID NO:4), 5 mM sodium phosphate buffer, 0.015% polysorbate, 20 mM sodium chloride, and 2.5% sucrose, at pH 6.2-6.3.

In another specific embodiment, the lyophilizable ophthalmic formulation comprises 20 mg/ml of the VEGF antagonist, 5 mM sodium phosphate buffer, 0.015% polysorbate, and 67.5 mM sodium chloride, pH about 6.2-6.3. In a more specific embodiment, the lyophilizable ophthalmic formulation consists essentially of 20 mg/ml of the VEGF antagonist (SEQ ID NO:4), 5 mM sodium phosphate buffer, 0.015% polysorbate, and 67.5 mM sodium chloride, pH 6.2-6.3.

In another specific embodiment, the lyophilizable ophthalmic formulation comprises 5 mg/ml, 10 mg/ml, or 40 mg/ml VEGF antagonist, 5 mM sodium phosphate buffer, 0.015% polysorbate, and 67.5 mM sodium chloride, pH about 6.2-6.3. In a more specific embodiment, the lyophilizable ophthalmic formulation consists essentially of 5 mg/ml, 10 mg/ml, or 40 mg/ml VEGF antagonist (SEQ ID NO:4), 5 mM sodium phosphate buffer, 0.015% polysorbate, and 67.5 mM sodium chloride, pH about 6.2-6.3.

Generally, the reconstituted formulation is about 2 times the concentration of the pre-lyophilized formulation, e.g., a 20 mg fusion protein/ml pre-lyophilized formulation is reconstituted to a final formulation of 40 mg fusion protein/ml.

Generally, the lyophilized formulation is reconstituted with sterile water suitable for injection. In one embodiment, the reconstitution liquid is bacteriostatic water.

In another aspect, the invention features a method of producing a lyophilized formulation of a VEGF-specific fusion protein antagonist, comprising subjecting the lyophilizable formulation of the invention to lyophilization to generate a lyophilized formulation. The lyophilized formulation may be lyophilized by any method known in the art for lyophilizing a liquid.

In another related aspect, the invention features a method of producing a reconstituted lyophilized formulation of a VEGF antagonist, comprising reconstituting the lyophilized formulation of the invention to a reconstituted formulation. In one embodiment, the reconstituted formulation is twice the concentration of the pre-lyophilized formulation, e.g., the method of the invention comprises: (a) producing a pre-lyophilized formulation of a VEGF-specific fusion protein antagonist, (b) subjecting the pre-lyophilized formulation of step (a) to lyophilization; and (c) reconstituting the lyophilized formulation of step (b).

The invention further features ophthalmic formulations provided in a pre-filled syringe or vial, particularly suitable for intravitreal administration.

Other objects and advantages will become apparent from a review of the ensuing detailed description.

DETAILED DESCRIPTION OF THE INVENTION

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

Unless stated otherwise, all technical and scientific terms and phrases used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference.

General Description

Safe handling and administration of formulations comprising proteins represent significant challenges to pharmaceutical formulators. Proteins possess unique chemical and physical properties that present stability problems: a variety of degradation pathways exist for proteins, implicating both chemical and physical instability. Chemical instability includes deamination, aggregation, clipping of the peptide backbone, and oxidation of methionine residues. Physical instability encompasses many phenomena, including, for example, aggregation and/or precipitation.

Chemical and physical stability can be promoted by removing water from the protein. Lyophilization (freeze-drying under controlled conditions) is commonly used for long-term storage of proteins. The lyophilized protein is substantially resistant to degradation, aggregation, oxidation, and other degenerative processes while in the freeze-dried state. The lyophilized protein may be reconstituted with water optionally containing a bacteriostatic preservative (e.g., benzyl alcohol) prior to administration.

DEFINITIONS

The term "carrier" includes a diluent, adjuvant, excipient, or vehicle with which a composition is administered. Carriers can include sterile liquids, such as, for example, water and oils, including oils of petroleum, animal, vegetable or synthetic origin, such as, for example, peanut oil, soybean oil, mineral oil, sesame oil and the like.

The term "excipient" includes a non-therapeutic agent added to a pharmaceutical composition to provide a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "lyophilized" or "freeze-dried" includes a state of a substance that has been subjected to a drying procedure such as lyophilization, where at least 90% of moisture has been removed, VEGF Antagonists A VEGF antagonist is a compound capable of blocking or inhibiting the biological action of vascular endothelial growth factor (VEGF), and includes fusion proteins capable of trapping VEGF. In a preferred embodiment, the VEGF antagonist is the fusion protein of SEQ ID NO:2 or 4; more preferably, SEQ ID NO:4. In specific embodiments, the VEGF antagonist is expressed in a mammalian cell line such as a CHO cell and may be modified post-translationally. In a specific embodiment, the fusion protein comprises amino acids 27-457 of SEQ ID NO:4 and is glycosylated at Asn residues 62, 94, 149, 222 and 308. Preferably, the VEGF antagonist is a dimer composed of two fusion proteins of SEQ ID NO:4.

The VEGF antagonist of the methods and formulations of the invention can be prepared by any suitable method known in the art, or that comes to be known. The VEGF antagonist is preferably substantially free of protein contaminants at the time it is used to prepare the pharmaceutically acceptable formulation. By "substantially free of protein contaminants" is meant, preferably, that at least 90% of the weight of protein of the VEGF-specific fusion protein antagonist preparation used for making a formulation is VEGF fusion protein antagonist protein, more preferably at least 95%, most preferably at least 99%. The fusion protein is preferably substantially free of aggregates. "Substantially free of aggregates" means that at least 90% of the weight of fusion protein is not present in an aggregate at the time the fusion protein is used to prepare the pharmaceutically effective formulation. Unless stated otherwise, the phosphates employed are sodium phosphates and a desired buffering pH is achieved by mixing appropriate amounts of mono- and dibasic sodium phosphate.

Stable Liquid Ophthalmic Formulations

In one aspect, the invention provides a stable pharmaceutically acceptable formulation comprising a VEGF antagonist, wherein the formulation is a liquid formulation suitable for ophthalmic use. Preferably, the liquid formulation comprises a pharmaceutically effective amount of the VEGF antagonist. The formulation can also comprise one or more pharmaceutically acceptable carriers, buffers, tonicity agents, stabilizers, and/or excipients. An example of a pharmaceutically acceptable liquid formulation comprises a VEGF antagonist in a pharmaceutically effective amount, a buffer, an organic co-solvent such as polysorbate, a tonicity agent such as NaCl, and optionally, a stabilizer such as sucrose or trehalose.

Stability is determined in a number of ways at specified time points, including determination of pH, visual inspection of color and appearance, determination of total protein content by methods known in the art, e.g., UV spectroscopy, and purity is determined by, for example, SDS-PAGE, size-exclusion HPLC, bioassay determination of activity, isoelectric focusing, and isoaspartate quantification. In one example of a bioassay useful for determining VEGF antagonist activity, a BAF/3 VEGFR1/EPOR cell line is used to determine VEGF165 binding by the VEGF antagonist of the invention.

Liquid formulations can be stored in an oxygen-deprived environment. Oxygen-deprived environments can be generated by storing the formulations under an inert gas such as, for example, nitrogen or argon. Liquid formulations are preferably stored at about 5° C.

Ophthalmic Lyophilized Formulations

In one aspect of the invention, an ophthalmically acceptable formulation comprising a VEGF antagonist is provided, wherein the formulation is a lyophilizable formulation. Lyophilizable formulations can be reconstituted into solutions, suspensions, emulsions, or any other suitable form for administration or use. Lyophilizable formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored below 25° C., for example, refrigerated at 2-8° C., or at room temperature (e.g., approximately 25° C.). Preferably, lyophilized formulations are stored below about 25° C., more preferably, at about 4-20° C.; below about 4° C.; below about −20° C.;

about −40° C.; about −70° C., or about −80° C. Stability of the lyophilized formulation may be determined in a number of ways known to the art, for example, by visual appearance of the cake and/or by moisture content.

Lyophilized formulations are typically reconstituted for use by addition of an aqueous solution to dissolve the lyophilized formulation. A wide variety of aqueous solutions can be used to reconstitute a lyophilized formulation. Preferably, lyophilized formulations are reconstituted using water. Lyophilized formulations are preferably reconstituted with a solution consisting essentially of water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used.

Freeze-dried or lyophilized formulations are typically prepared from liquids, that is, from solutions, suspensions, emulsions, and the like. Thus, the liquid that is to undergo freeze-drying or lyophilization preferably comprises all components desired in a final reconstituted liquid formulation. As a result, when reconstituted, the freeze-dried or lyophilized formulation will render a desired liquid formulation upon reconstitution.

EXAMPLES

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only to the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

Example 1

Stability of 50 mg/ml VEGF Trap Liquid Formulation Stored at 5° C. in 3 ml Glass Vials An ophthalmic liquid formulation containing 50 mg/ml VEGF Trap (SEQ ID NO:4), 10 mM phosphate, 50 mM NaCl, 0.1% polysorbate 20, 5% sucrose, and pH 6.25, was stored at 5° C. in 3 ml glass vials and samples tested at 3, 6, 9, 12, 18 and 24 months. Stability was determined by SE-HPLC. The results are shown in Table 1. Turbidity was measured at $OD_{405}$ nm; and percent recovered protein and purity by size exclusion HPLC.

TABLE 1

Stability of 50 mg/ml VEGF Trap Protein (VGFT-SS065)

| Months | Visual Appearance | Turbidity ($OD_{405}$ nm) | pH | % VEGF Trap Recovered | % VEGF Trap Native Configuration |
|---|---|---|---|---|---|
| 0 | Pass | 0.00 | 6.2 | 100 | 98.8 |
| 3 | Pass | 0.00 | 6.2 | 101 | 98.7 |
| 6 | Pass | 0.01 | 6.3 | 100 | 98.3 |
| 9 | Pass | 0.01 | 6.3 | 101 | 98.3 |
| 12 | Pass | 0.01 | 6.3 | 104 | 98.4 |
| 18 | Pass | 0.01 | 6.3 | 96 | 98.1 |
| 24 | Pass | 0.01 | 6.3 | 105 | 98.1 |

Example 2

Stability of 50 mg/ml VEGF Trap Liquid Formulation Stored at 5° C. in 3 ml Glass Vials A liquid formulation containing 50 mg/ml VEGF Trap (SEQ ID NO:4), 10 mM phosphate, 50 mM NaCl, 3% polyethylene glycol 3350, 5% sucrose, and pH 6.25, was stored at 5° C. in 3 ml glass vials and samples tested at 3, 6, 9, 12, 18 and 24 months. Stability results are shown in Table 2. Turbidity, percent recovered protein and purity was determined as described above.

TABLE 2

Stability of 50 mg/ml VEGF Trap Protein (VGFT-SS065)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 98.9 |
| 3 | Pass | 0.00 | 6.1 | 104 | 98.5 |
| 6 | Pass | 0.01 | 6.3 | 99 | 98.3 |
| 9 | Pass | 0.00 | 6.3 | 102 | 97.6 |
| 12 | Pass | 0.01 | 6.3 | 103 | 98.0 |
| 18 | Pass | 0.00 | 6.3 | 113 | 97.7 |
| 24 | Pass | 0.00 | 6.2 | 106 | 97.6 |

Example 3

Stability of 40 mg/ml VEGF Trap Liquid Formulation Stored at 5° C. in 3 ml Glass Vials A liquid formulation containing 40 mg/ml VEGF Trap (SEQ ID NO:4), 10 mM phosphate, 40 mM NaCl, 0.03% polysorbate 20, 5% sucrose, and pH 6.3, was stored at 5° C. in 3 ml glass vials and samples tested at 0.5, 1, 2, 3, and 4 months. Stability results are shown in Table 3. Turbidity, percent recovered protein and purity was determined as described above.

TABLE 3

Stability of 40 mg/ml VEGF Trap Protein (VGFT-SS207)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.5 |
| 0.5 | Pass | 0.00 | 6.3 | 99 | 99.4 |
| 1 | Pass | 0.00 | 6.2 | 98 | 99.5 |
| 2 | Pass | 0.00 | 6.2 | 95 | 99.2 |
| 3 | Pass | 0.01 | 6.4 | | |
| 4 | Pass | 0.01 | 6.3 | | |

Example 4

Stability of 40 mg/ml VEGF Trap Liquid Formulation Stored at 5° C. in Pre-Filled Glass Syringe A liquid formulation containing 40 mg/ml VEGF trap (SEQ ID NO:4), 10 mM phosphate, 40 mM NaCl, 0.03% polysorbate 20, 5% sucrose, and pH 6.3, was stored at 5° C. in 1 ml prefilled luer glass syringe with 4023/50 FLUROTEC™ coated (elastomer coated) plunger and samples tested at 0.5, 1, 2, 3, and 4 months. Stability results are shown in Table 4. Turbidity, percent recovered protein and purity was determined as described above.

TABLE 4

Stability of 40 mg/ml VEGF Trap Protein (VGFT-SS207)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.4 |
| 0.5 | Pass | 0.00 | 6.3 | 100 | 99.3 |
| 1 | Pass | 0.00 | 6.3 | 100 | 99.4 |
| 2 | Pass | 0.00 | 6.3 | 97 | 99.1 |
| 3 | Pass | 0.01 | 6.4 | | |
| 4 | Pass | 0.01 | 6.3 | | |

Example 5

Stability of 40 mg/ml VEGF Trap Liquid Formulation Stored at 5° C. in 3 ml Glass Vials A liquid formulation containing 40 mg/ml VEGF trap (SEQ ID NO:4), 10 mM phosphate, 135 mM NaCl, 0.03% polysorbate 20, and pH 6.3, was stored at 5° C. in 3 ml glass vials and samples tested at 0.5, 1, 2, 3, and 4 months. Stability results are shown in Table 5. Turbidity, percent recovered protein and purity was determined as described above.

TABLE 5

Stability of 40 mg/ml VEGF Trap Protein (VGFT-SS203)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.3 |
| 0.5 | Pass | 0.00 | 6.2 | 87 | 99.2 |
| 1 | Pass | 0.00 | 6.2 | 88 | 99.1 |
| 2 | Pass | 0.00 | 6.3 | 103 | 99.2 |
| 3 | Pass | 0.00 | 6.3 | 88 | 99.0 |
| 4 | Pass | 0.00 | 6.2 | 85 | 98.9 |
| 5 | Pass | 0.00 | 6.3 | 84 | 99.0 |

Example 6

Stability of 40 mg/ml VEGF Trap Liquid Formulation Stored at 5° C. in 1 ml Pre-Filled Glass Syringe A liquid formulation containing 40 mg/ml VEGF trap (SEC) ID NO:4), 10 mM phosphate, 135 mM NaCl, 0.03% polysorbate 20, and pH 6.3, was stored at 5° C. in 1 ml prefilled glass luer syringe with 4023/50 FLUROTEC™ coated (elastomer coated) plunger and samples tested at 0.5, 1, 2, 3, 4, and 5 months. Stability results are shown in Table 6. Turbidity, percent recovered protein and purity was determined as described above.

TABLE 6

Stability of 40 mg/ml VEGF Trap Protein (VGFT-SS203)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.2 |
| 0.5 | Pass | 0.01 | 6.3 | 101 | 99.2 |
| 1 | Pass | 0.00 | 6.3 | 101 | 99.2 |
| 2 | Pass | 0.00 | 6.3 | — | — |
| 3 | Pass | 0.01 | 6.3 | 102 | 99.1 |
| 4 | Pass | 0.01 | 6.3 | 103 | 98.8 |
| 5 | Pass | 0.00 | 6.3 | 99 | 98.9 |

Example 7

Stability of Lyophilized 20 mg/ml VEGF Trap Formulation Stored at 5° C. in 3 ml Glass Vials and Reconstituted to 40 mg/ml 0.8 ml of a liquid formulation containing 20 mg/ml VEGF trap (SEQ ID NO:4), 5 mM phosphate, 20 mM NaCl, 0.015% polysorbate 20, 2.5% sucrose, and pH 6.3, were lyophilized in 3 ml glass vials. Samples were stored at 5° C. and tested at 1, and 2 months. VEGF trap was reconstituted to a final concentration of 40 mg/ml VEGF Trap (final volume of 0.4 ml). Stability results are shown in Table 7 (t=time in months; *=visual appearance; **=reconstitution time). Turbidity, percent recovered protein and purity was determined as described above.

TABLE 7

Stability of Lyophilized 20 mg/ml VEGF Trap Protein (VGFT-SS216)

| t | Vis. App.* | Recon. Time** (min) | Vis. App.* Reconst'd Liquid | Turbidity | pH | % VEGF Trap Recovered | % VEGF Trap Native Config. |
|---|---|---|---|---|---|---|---|
| 0 | Pass | 0.6 | Pass | 0.00 | 6.3 | 100 | 99.5 |
| 1 | Pass | 0.6 | Pass | 0.01 | 6.3 | 106 | 99.4 |
| 2 | Pass | 0.4 | Pass | 0.01 | 6.2 | 103 | 99.3 |

Example 8

Stability of Lyophilized 20 mg/ml VEGF Trap Formulation Stored at 5° C. in 3 ml Glass Vials 0.8 ml of a liquid formulation containing 20 mg/ml VEGF trap (SEQ ID NO:4), 5 mM phosphate, 67.5 mM NaCl, 0.015% polysorbate 20, and pH 6.3, were lyophilized in 3 ml glass vials. Samples were stored at 5° C. and tested at 1, 2, and 3 months. VEGF trap was reconstituted to a final concentration of 40 mg/ml VEGF trap (final volume of 0.4 ml). Stability results are shown in Table 8 (t=time in months; *=visual appearance; **=reconstitution time).

TABLE 8

Stability of Lyophilized 20 mg/ml VEGF Trap Protein (VGFT-SS216)

| t | Vis. App.* | Recon. Time** (min) | Vis. App.* Reconst'd Liquid | Turbidity | pH | % VEGF Trap Recovered | % VEGF Trap Native Config. |
|---|---|---|---|---|---|---|---|
| 0 | Pass | 0.7 | Pass | 0.00 | 6.3 | 100 | 99.0 |
| 1 | Pass | 0.7 | Pass | 0.01 | 6.2 | 105 | 98.9 |
| 2 | Pass | 0.4 | Pass | 0.01 | 6.2 | 103 | 98.9 |

We claim:

1. A stable liquid ophthalmic formulation of a vascular endothelial growth factor (VEGF) antagonist, comprising:
   (a) between 50 mg/ml to about 10 mg/ml of a VEGF antagonist comprising amino acids 27-475 of SEQ ID NO:4;
   (b) about 0.03% to about 0.1% polysorbate;
   (c) about 5-40 mM of sodium phosphate buffer, pH of about 5.8 to about 7.0; and
   (d) either:
      (i) about 5% sucrose and about 40 to about 50 mM NaCl, or
      (ii) about 135 mM NaCl,
wherein at least 99% of the VEGF antagonist is present in native conformation following storage at 5° C. for 2 months as measured by size exclusion chromatography.

2. The formulation of claim 1, comprising between 50 mg/ml to about 10 mg/ml of the VEGF antagonist, about 10 mM sodium phosphate buffer, about 40 mM NaCl, about 0.03% polysorbate, and about 5% sucrose, pH about 6.2-6.3.

3. The formulation of claim 2, comprising about 10 to about 40 mg/ml of the VEGF antagonist.

4. The formulation of claim 3, comprising VEGF antagonist at a concentration of about 10 mg/ml.

5. The formulation of claim 3, comprising VEGF antagonist at a concentration of about 40 mg/ml.

6. The formulation of claim 1, comprising between 50 mg/ml to about 10 mg/ml of the VEGF antagonist, about 10 mM sodium phosphate buffer, about 135 mM NaCl and about 0.03% polysorbate, pH about 6.2-6.3.

7. The formulation of claim 6, comprising about 10 to about 40 mg/ml of the VEGF antagonist.

8. The formulation of claim 7, comprising VEGF antagonist at a concentration of about 10 mg/ml.

9. The formulation of claim 7, comprising VEGF antagonist at a concentration of about 40 mg/ml.

10. A pre-filled syringe suitable for intravitreal administration comprising the formulation of claim 1.

11. A pre-filled syringe suitable for intravitreal administration comprising the formulation of claim 4.

12. A pre-filled syringe suitable for intravitreal administration comprising the formulation of claim 5.

13. A pre-filled syringe suitable for intravitreal administration comprising the formulation of claim 6.

14. A pre-filled syringe suitable for intravitreal administration comprising the formulation of claim 8.

15. A pre-filled syringe suitable for intravitreal administration comprising the formulation of claim 9.

16. A non-liquid formulation of a vascular endothelial growth factor (VEGF) antagonist made according to the steps of:
   (a) combining in a liquid solution the following excipients:
      (i) about 5-50 mg/ml of the VEGF antagonist, comprising amino acids 27-475 of SEQ ID NO:4;
      (ii) about 5-25 mM of sodium phosphate buffer, pH about 5.8-7.0;
      (iii) about 0.01-0.15% of an organic co-solvent, selected from the group consisting of polysorbate, polyethylene glycol (PEG), propylene glycol, and a combination thereof; and
      (iv) about 1-10% of a stabilizing agent selected from the group consisting of sucrose, sorbitol, glycerol, trehalose, and mannitol; and
   (b) lyophilizing the combination of step (a),
wherein at least about 99% of the VEGF antagonist is present in native conformation as measured by size exclusion chromatography following storage at 5° C. for 2 months.

17. The non-liquid formulation of claim 16, wherein about 20 mg/ml of the VEGF antagonist, about 5 mM sodium phosphate buffer, about 0.015% polysorbate, about 2.5% sucrose, and about 20 mM sodium chloride, pH about 6.2-6.3 are combined at step (a).

18. The non-liquid formulation of claim 16, wherein about 20 mg/ml of the VEGF antagonist, about 5 mM sodium phosphate buffer, about 0.015% polysorbate, and about 67.5 mM sodium chloride, pH about 6.2-6.3 are combined at step (a).

19. The non-liquid formulation of claim 16, wherein the formulation can be reconstituted in about 0.7 minutes or less.

* * * * *

UNITED STATES PATENT AND TRADEMARK OFFICE
CERTIFICATE OF CORRECTION

PATENT NO. : 8,092,803 B2  
APPLICATION NO. : 12/833417  
DATED : January 10, 2012  
INVENTOR(S) : Eric Furfine et al.

Page 1 of 1

It is certified that error appears in the above-identified patent and that said Letters Patent is hereby corrected as shown below:

Column 19, claim 1, line 5, that portion of the line reading "amino acids 27-475" should read --amino acids 27-457--.

Column 20, claim 16, line 14, that portion of the line reading "amino acids 27-475" should read --amino acids 27-457--.

Signed and Sealed this  
Ninth Day of April, 2013

Teresa Stanek Rea  
*Acting Director of the United States Patent and Trademark Office*

SEQUENCE LISTING

<160> NUMBER OF SEQ ID NOS: 4

<210> SEQ ID NO 1
<211> LENGTH: 1453
<212> TYPE: DNA
<213> ORGANISM: Artificial Sequence
<220> FEATURE:
<223> OTHER INFORMATION: Synthetic

<400> SEQUENCE: 1

```
aagcttgggc tgcaggtcga tcgactctag aggatcgatc cccgggcgag ctcgaattcg      60
caaccaccat ggtcagctac tgggacaccg ggtcctgct gtgcgcgctg ctcagctgtc     120
tgcttctcac aggatctagt tccggaggta gacctttcgt agagatgtac agtgaaatcc     180
ccgaaattat acacatgact gaaggaaggg agctcgtcat tccctgccgg gttacgtcac     240
ctaacatcac tgttacttta aaaaagtttc cacttgacac tttgatccct gatggaaaac     300
gcataatctg ggacagtaga aagggcttca tcatatcaaa tgcaacgtac aagaaaatag     360
ggcttctgac ctgtgaagca acagtcaatg gcatttgta taagcaaac tatctcacac     420
atcgacaaac caatacaatc atagatgtgg ttctgagtcc gtctcatgga attgaactat     480
ctgttggaga aaagcttgtc ttaaattgta cagcaagaac tgaactaaat gtggggattg     540
acttcaactg ggaatacct tcttcgaagc atcagcataa gaaacttgta aaccgagacc     600
taaaaaccca gtctgggagt gagatgaaga aattttttga gcaccttaact atagatggtg     660
taacccggag tgaccaagga ttgtacacct gtgcagcatc cagtgggctg atgaccaaga     720
agaacagcac atttgtcagg gtccatgaaa agggcccggg cgacaaaact cacacatgcc     780
caccgtgccc agcacctgaa ctcctggggg gaccgtcagt cttcctcttc cccccaaaac     840
ccaaggacac cctcatgatc tcccggaccc ctgaggtcac atgcgtggtg gtggacgtga     900
gccacgaaga ccctgaggtc aagttcaact ggtacgtgga cggcgtggag gtgcataatg     960
ccaagacaaa gccgcgggag gagcagtaca acagcacgta ccgtgtggtc agcgtcctca    1020
ccgtcctgca ccaggactgg ctgaatggca aggagtacaa gtgcaaggtc tccaacaaag    1080
ccctcccagc ccccatcgag aaaaccatct ccaaagccaa agggcagccc cgagaaccac    1140
aggtgtacac cctgccccca tcccgggatg agctgaccaa gaaccaggtc agcctgacct    1200
gcctggtcaa aggcttctat cccagcgaca tcgccgtgga gtgggagagc aatgggcagc    1260
cggagaacaa ctacaagacc acgcctcccg tgctggactc cgacggctcc ttcttcctct    1320
atagcaagct caccgtggac aagagcaggt ggcagcaggg gaacgtcttc tcatgctccg    1380
tgatgcatga ggctctgcac aaccactaca cgcagaagag cctctccctg tctccgggta    1440
aatgagcggc cgc                                                       1453
```

<210> SEQ ID NO 2
<211> LENGTH: 458
<212> TYPE: PRT
<213> ORGANISM: Artificial Sequence
<220> FEATURE:
<223> OTHER INFORMATION: Synthetic

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Gly Arg Pro Phe Val Glu
            20                  25                  30
```

-continued

Met Tyr Ser Glu Ile Pro Glu Ile Ile His Met Thr Glu Gly Arg Glu
        35                  40                  45

Leu Val Ile Pro Cys Arg Val Thr Ser Pro Asn Ile Thr Val Thr Leu
 50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
                100                 105                 110

Thr Asn Tyr Leu Thr His Arg Gln Thr Asn Thr Ile Ile Asp Val Val
            115                 120                 125

Leu Ser Pro Ser His Gly Ile Glu Leu Ser Val Gly Glu Lys Leu Val
130                 135                 140

Leu Asn Cys Thr Ala Arg Thr Glu Leu Asn Val Gly Ile Asp Phe Asn
145                 150                 155                 160

Trp Glu Tyr Pro Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
450                 455

-continued

<210> SEQ ID NO 3
<211> LENGTH: 1377
<212> TYPE: DNA
<213> ORGANISM: Artificial Sequence
<220> FEATURE:
<223> OTHER INFORMATION: Synthetic

<400> SEQUENCE: 3

```
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata gaaacttgt aaaccgagac      540
ctaaaaaccc agtctgggag tgagatgaag aaatttttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aaagggcagc cccgagaacc acaggtgtac    1080
accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga      1377
```

<210> SEQ ID NO 4
<211> LENGTH: 458
<212> TYPE: PRT
<213> ORGANISM: Artificial Sequence
<220> FEATURE:
<223> OTHER INFORMATION: Synthetic

<400> SEQUENCE: 4

```
Met Val Ser Tyr Trp Asp Thr Gly Val Leu Leu Cys Ala Leu Leu Ser
  1               5                  10                  15

Cys Leu Leu Leu Thr Gly Ser Ser Ser Gly Ser Asp Thr Gly Arg Pro
             20                  25                  30

Phe Val Glu Met Tyr Ser Glu Ile Pro Glu Ile Ile His Met Thr Glu
         35                  40                  45

Gly Arg Glu Leu Val Ile Pro Cys Arg Val Thr Ser Pro Asn Ile Thr
     50                  55                  60

Val Thr Leu Lys Lys Phe Pro Leu Asp Thr Leu Ile Pro Asp Gly Lys
 65                  70                  75                  80
```

-continued

```
Arg Ile Ile Trp Asp Ser Arg Lys Gly Phe Ile Ser Asn Ala Thr
                 85                  90                  95
Tyr Lys Glu Ile Gly Leu Leu Thr Cys Glu Ala Thr Val Asn Gly His
            100                 105                 110
Leu Tyr Lys Thr Asn Tyr Leu Thr His Arg Gln Thr Asn Thr Ile Ile
        115                 120                 125
Asp Val Val Leu Ser Pro Ser His Gly Ile Glu Leu Ser Val Gly Glu
    130                 135                 140
Lys Leu Val Leu Asn Cys Thr Ala Arg Thr Glu Leu Asn Val Gly Ile
145                 150                 155                 160
Asp Phe Asn Trp Glu Tyr Pro Ser Ser Lys His Gln His Lys Lys Leu
                165                 170                 175
Val Asn Arg Asp Leu Lys Thr Gln Ser Gly Ser Glu Met Lys Lys Phe
            180                 185                 190
Leu Ser Thr Leu Thr Ile Asp Gly Val Thr Arg Ser Asp Gln Gly Leu
        195                 200                 205
Tyr Thr Cys Ala Ala Ser Ser Gly Leu Met Thr Lys Lys Asn Ser Thr
    210                 215                 220
Phe Val Arg Val His Glu Lys Asp Lys Thr His Thr Cys Pro Pro Cys
225                 230                 235                 240
Pro Ala Pro Glu Leu Leu Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
        275                 280                 285
Tyr Val Asp Gly Val Glu Val His Asn Ala Lys Thr Lys Pro Arg Glu
    290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
            340                 345                 350
Gln Pro Arg Glu Pro Gln Val Tyr Thr Leu Pro Pro Ser Arg Asp Glu
        355                 360                 365
Leu Thr Lys Asn Gln Val Ser Leu Thr Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly Lys
    450                 455
```